(12) United States Patent
Gono et al.

(10) Patent No.: US 9,131,847 B2
(45) Date of Patent: Sep. 15, 2015

(54) METHOD AND APPARATUS FOR DETECTING ABNORMAL LIVING TISSUE

(75) Inventors: Kazuhiro Gono, Sagamihara (JP); Takeshi Suga, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 694 days.

(21) Appl. No.: 12/132,932

(22) Filed: Jun. 4, 2008

(65) Prior Publication Data

US 2009/0306522 A1 Dec. 10, 2009

(51) Int. Cl.
*A61B 6/00* (2006.01)
*A61B 5/00* (2006.01)
*A61B 5/026* (2006.01)
*A61B 1/00* (2006.01)

(52) U.S. Cl.
CPC ........... *A61B 5/0075* (2013.01); *A61B 1/00087* (2013.01); *A61B 5/0084* (2013.01); *A61B 5/026* (2013.01); *A61B 1/00135* (2013.01)

(58) Field of Classification Search
CPC ..... A61B 1/0661; A61B 1/06; A61B 1/00163
USPC ......... 600/473, 476, 478, 106, 160, 178, 310, 600/325, 327, 332, 339; 356/316, 364, 369, 356/479
See application file for complete search history.

(56) References Cited

U.S. PATENT DOCUMENTS

| | | | |
|---|---|---|---|
| 4,292,961 A | 10/1981 | Kawashima | |
| 4,648,892 A * | 3/1987 | Kittrell et al. | 65/387 |
| 4,998,973 A | 3/1991 | Kikuchi | |
| 5,329,922 A * | 7/1994 | Atlee, III | 600/328 |
| 5,353,783 A * | 10/1994 | Nakao et al. | 600/106 |
| 5,365,925 A | 11/1994 | Lee | |
| 5,547,455 A * | 8/1996 | McKenna et al. | 600/113 |
| 5,604,531 A | 2/1997 | Iddan et al. | |
| 5,833,603 A | 11/1998 | Kovacs et al. | |
| 6,030,365 A * | 2/2000 | Laufer | 604/164.01 |
| 6,104,941 A * | 8/2000 | Huey et al. | 600/376 |
| 6,226,540 B1 * | 5/2001 | Bernreuter | 600/323 |
| 6,393,311 B1 | 5/2002 | Edgar, Jr. et al. | |
| 6,516,209 B2 | 2/2003 | Cheng et al. | |
| 6,639,674 B2 | 10/2003 | Sokolov et al. | |
| 6,640,117 B2 | 10/2003 | Makarewicz et al. | |
| 6,692,494 B1 | 2/2004 | Cooper et al. | |
| 6,738,654 B2 | 5/2004 | Sohrab | |

(Continued)

FOREIGN PATENT DOCUMENTS

CN 1509152 6/2004
CN 1678239 10/2005

(Continued)

OTHER PUBLICATIONS

The Japanese Office Action, issued on Feb. 28, 2012, in the corresponding Japanese application No. 2010-547769.

(Continued)

*Primary Examiner* — Joel F Brutus

(57) ABSTRACT

Light scattering and absorption techniques for the detection of possible abnormal living tissue. Apparatus and methods for utilizing multiple blood content detection sensors and/or contact sensors for beneficially providing data to better guide an endoscope or colonoscope to locate abnormal tissue, tumors, or tissues that precede the development of such lesions or tumors.

23 Claims, 11 Drawing Sheets

(56) References Cited

U.S. PATENT DOCUMENTS

| | | | |
|---|---|---|---|
| 6,876,448 | B2 | 4/2005 | Imura et al. |
| 6,951,536 | B2 | 10/2005 | Yokoi et al. |
| 7,118,529 | B2 | 10/2006 | Glukhovsky et al. |
| 7,468,044 | B2 | 12/2008 | Iddan |
| 7,492,935 | B2 | 2/2009 | Glukhovsky |
| 7,561,908 | B2 | 7/2009 | Glukhovsky et al. |
| 7,618,376 | B2 | 11/2009 | Kimball |
| 7,637,864 | B2 | 12/2009 | Yokoi et al. |
| 7,704,205 | B2 | 4/2010 | Mizuno |
| 7,724,928 | B2 | 5/2010 | Glukhovsky et al. |
| 7,792,344 | B2 | 9/2010 | Wang et al. |
| 7,914,442 | B1 | 3/2011 | Gazdzinski |
| 2002/0026098 | A1* | 2/2002 | Kobayashi ............ 600/160 |
| 2002/0042562 | A1 | 4/2002 | Meron et al. |
| 2002/0111544 | A1 | 8/2002 | Iddan |
| 2002/0115908 | A1* | 8/2002 | Farkas et al. ............ 600/178 |
| 2002/0177779 | A1 | 11/2002 | Adler et al. |
| 2003/0085994 | A1 | 5/2003 | Fujita et al. |
| 2003/0130577 | A1* | 7/2003 | Purdy et al. ............ 600/433 |
| 2004/0176672 | A1* | 9/2004 | Silver et al. ............ 600/345 |
| 2004/0215068 | A1 | 10/2004 | Lykke et al. |
| 2004/0249245 | A1 | 12/2004 | Irion |
| 2004/0249291 | A1 | 12/2004 | Honda et al. |
| 2005/0033276 | A1 | 2/2005 | Adachi |
| 2005/0075551 | A1 | 4/2005 | Horn et al. |
| 2005/0085696 | A1 | 4/2005 | Uchiyama et al. |
| 2005/0148847 | A1 | 7/2005 | Uchiyama et al. |
| 2005/0267340 | A1 | 12/2005 | Ishihara |
| 2006/0178557 | A1 | 8/2006 | Mintchev et al. |
| 2006/0281983 | A1* | 12/2006 | Al-Ali et al. ............ 600/323 |
| 2007/0088220 | A1 | 4/2007 | Stahmann |
| 2007/0106147 | A1 | 5/2007 | Altmann et al. |
| 2007/0129615 | A1 | 6/2007 | Backman et al. |
| 2007/0179368 | A1* | 8/2007 | Backman et al. ............ 600/315 |
| 2007/0244402 | A1 | 10/2007 | Brockway et al. |
| 2008/0125623 | A1 | 5/2008 | Tamura et al. |
| 2008/0200784 | A1* | 8/2008 | Cheng ............ 600/322 |
| 2009/0312618 | A1 | 12/2009 | Hengerer et al. |

FOREIGN PATENT DOCUMENTS

| | | |
|---|---|---|
| EP | 1695662 | 8/2006 |
| JP | 5-115463 | 5/1993 |
| JP | 2001-204685 | 7/2001 |
| JP | 2003-506132 | 2/2003 |
| JP | 2005-328990 | 12/2005 |
| JP | 2007-51879 | 3/2007 |
| KR | 10-2003-0071820 | 9/2003 |
| KR | 10-2005-0095639 | 9/2005 |
| KR | 10-2007-0047221 | 5/2007 |
| WO | 94/21173 | 9/1994 |
| WO | 02055984 | 7/2002 |
| WO | 02073507 | 9/2002 |
| WO | 2004032621 | 4/2004 |
| WO | 2005039402 | 5/2005 |
| WO | 2005113021 | 12/2005 |
| WO | 2007041542 | 4/2007 |
| WO | 2007113165 | 10/2007 |

OTHER PUBLICATIONS

The Chinese Office Action, issued on May 25, 2011, in related Chinese patent application No. 200880115162.2.

The International Search Report & Written Opinion, issued on Apr. 24, 2009, in related PCT application No. PCT/JP2008/070825.

The International Search Report & Written Opinion, issued on Mar. 3, 2009, in related PCT application No. PCT/PCT/JP2008/070962.

The International Search Report & Written Opinion, issued on Mar. 5, 2009, in related PCT application No. PCT/JP2008/070827.

The International Search Report & Written Opinion, issued on Sep. 15, 2009, in related PCT application No. PCT/JP2009/060570.

The International Search Report & Written Opinion, issued on Jul. 21, 2009, in related PCT application No. PCT/JP2009/061790.

A Katzir, "Biometrical Fiberoptic Sensors," 1988, Optical Society of America, 1988 Technical Digest Series, vol. 2, pp. 4-6.

The Office Actions mailed on Mar. 26, 2010, Sep. 14, 2010, Dec. 9, 2010, May 9, 2011 and Oct. 24, 2011, in related U.S. Appl. No. 12/171,505.

The Office Actions mailed on Sep. 16, 2011, Dec. 29, 2011 and Mar. 15, 2012, in related U.S. Appl. No. 11/937,185.

The Office Actions mailed on Dec. 28, 2010, Jun. 2, 2011, Oct. 18, 2011 and Dec. 29, 2011, in related U.S. Appl. No. 11/937,153.

The Office Actions mailed on Apr. 28, 2011, Nov. 14, 2011 and Mar. 5, 2012, in related U.S. Appl. No. 11/937,133.

The extended European Search Report by the European Patent Office, issued on Aug. 1, 2013, in the related European Patent Application No. 09758454.4.

* cited by examiner

METHOD AND APPARATUS FOR DETECTING ABNORMAL LIVING TISSUE

CROSS REFERENCE TO RELATED APPLICATIONS

This application is related to U.S. patent application Ser. No. 11/937,133, filed on Nov. 8, 2007, entitled "Blood Content Detecting Capsule."

FIELD OF THE INVENTION

The present invention relates generally to the utilization of light scattering and absorption techniques to detect possible abnormal living tissue. More specifically, the invention relates to an apparatus and method for utilizing multiple blood content sensors to guide a probe or endoscope to more advantageously detect abnormal tissue within a living body.

BACKGROUND OF THE INVENTION

Scientists have discovered that a detectible increase in the blood content of superficial mucous membrane occurs proximate cancerous and precancerous lesions in the colon relative to the blood content of healthy tissue as described in, for example, R K Wali, H K Roy, Y L Kim, Y Liu, J L Koetsier, D P Kunte, M J Goldberg, V Turzhitsky and V Backman, *Increased Microvascular Blood Content is an Early Event in Colon Carcinogenesis*, Gut Vol. 54, pp 654-660 (2005), which is incorporated by reference herein. This phenomenon is referred to as early increase in blood supply (EIBS).

Relying on this phenomenon, it has been discovered that it is possible to predict an area of potential abnormality based on early increase in blood supply (EIBS) in the area of abnormality. Further, it has been discovered, that by using a probe applying collimated light to an area of interest, and detecting the amount of absorbed and reflected light it is possible to provide information to a clinician to guide an endoscope to detect a possible abnormality in vivo without an invasive procedure. Such techniques have been described for example in U.S. patent application Ser. No. 11/937,133 filed on Nov. 8, 2007, entitled "Blood Content Detecting Capsule", assigned to the assignee of the present invention, which is incorporated by reference herein.

However, particular types of optical blood content sensors require contact between the detection sensors and the mucosa of the underlying tissue for accurate detection of blood content. When a gap is present between these detection sensor types and the tissue of interest, a reduced amplitude of light interacted with the illuminated tissue will be received by the sensor and may be of little value in detecting abnormalities. Accordingly, in order to improve the likelihood that an abnormal area of tissue will be detected, it is important to ensure that the measurement sensor remains in contact with the tissue under investigation. Prior contemplated configurations have not addressed this issue. As a result, areas of abnormality may be missed or not detected with such systems.

SUMMARY OF THE INVENTION

The present invention advantageously increases data accuracy from detection sensors based on systems and methods that increase the desired sensor contact and/or identify collected data during the instances when such contact with the tissue under investigation occurs. This increase is accomplished in the present invention by employing, for example, contact detectors associated with the blood content detectors as part of a probe for insertion into a cavity of a living body, such as an endoscope or endoscopic sheath, and/or employing multiple blood content detectors for beneficially providing data to better guide an endoscope, colonoscope, or other probe, to locate abnormal tissue, tumors, or tissues that precede the development of such lesions or tumors.

In one aspect of the invention, contact detectors are employed with optical blood content detectors that provide more accurate blood content data when such sensors are in direct contact with the subject tissue. The contact detectors beneficially indicate when such sensors are in contact with tissue and correspondingly indicate that the generated blood content information signals at that instance are more likely to have improved accuracy than during instances when such sensors are not in contact with tissue. Further, the contact sensors may generate signals or power to the blood content sensors such that the illuminators and collectors within the blood content sensors are energized or powered on only during periods when the contact sensors are in contact with the tissue mucosa.

In another aspect of the invention, improved blood content detection is achieved by the use of multiple blood content sensors advantageously positioned in or on the surface of the probe or endoscope. The detection and locating of abnormal tissue is enhanced based on the blood detection data from the multiple sensors. It is particularly advantageous to use substantially simultaneously generated data from such sensors which can be statistically processed or otherwise to better and more accurately provide information for use in guiding the probe or endoscope.

BRIEF DESCRIPTION OF THE DRAWINGS

For a better understanding of the present invention, reference is made to the following description and accompanying drawings, while the scope of the invention is set forth in the appended claims:

DETAILED DESCRIPTION

Figure 1:
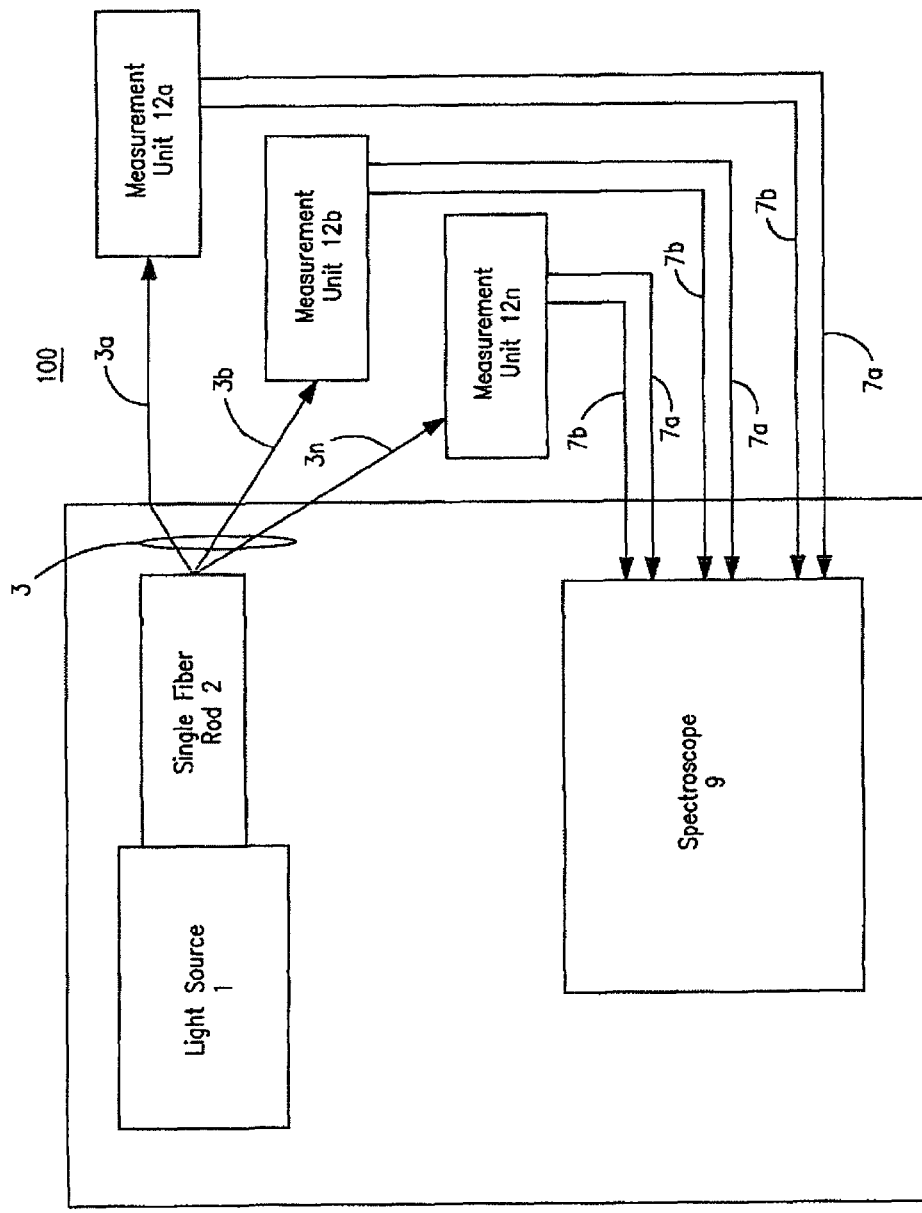
FIG. 1 illustrates a block diagram of an exemplary system in accordance with one aspect of the invention utilizing multiple blood content detector sensors.

The present invention relates generally to improvements in blood flow detection due to the improved contact and possibility of improved contact between the various detection sensors and the living tissue mucosa under investigation.

Referring to the drawings, like numbers indicate like parts throughout the views as used in the description herein, the meaning of "a" "an," and "the" includes plural reference unless the context clearly dictates otherwise. Also, as used in the description herein, the meaning of "in" includes both "in" and "on" unless the context clearly dictates otherwise. Also, as used in the description herein, the meanings of "and" and "or" include both the conjunctive and disjunctive and may be used interchangeably unless the context clearly dictates otherwise.

FIG. 1 depicts a schematic diagram of blood detection system 100 containing three detection sensors.

However, as will be appreciated by those skilled in the art, the number of detection sensors or windows is not limited to three. Light source 1 is in contact with single fiber rod 2. The light emanating from light source 1 is focused on the end face of single fiber rod 2. Due to the internal configuration of single fiber rod 2, the beams of light are repeatedly reflected off the inner walls of the single fiber's core resulting in a light source of uniform intensity, i.e., collimated light.

Figure 3:
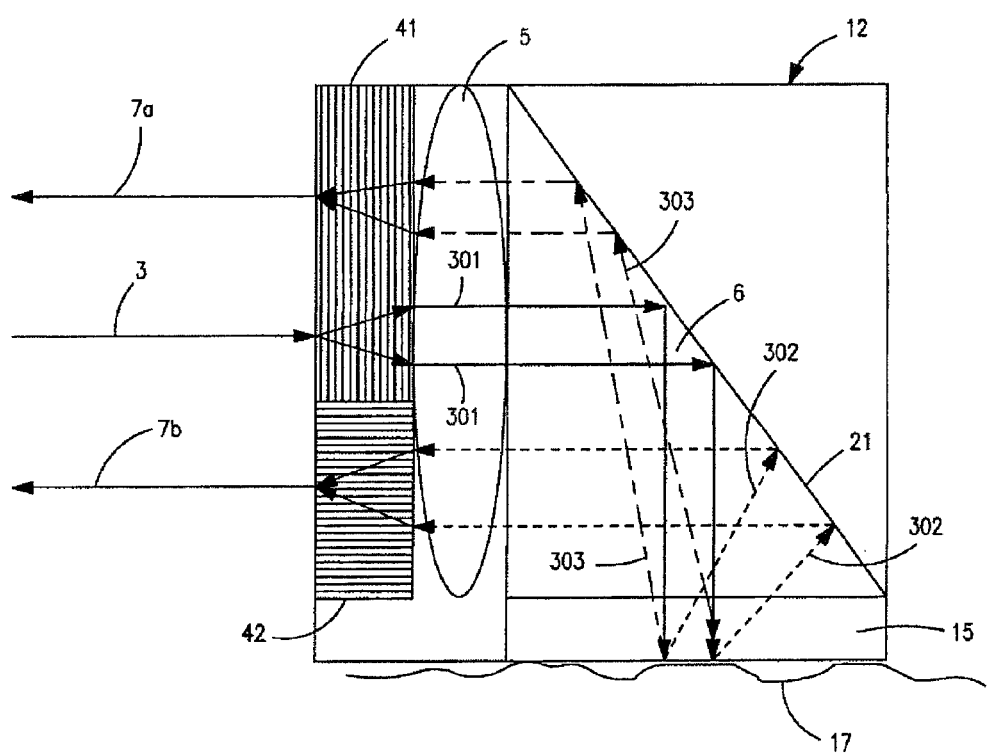
FIG. 3 illustrates an exemplary embodiment of an optical blood content sensor useable with the present invention.

Single fiber rod 2 is further in contact with fiber bundle 3. Fiber bundle 3 is made up of the independent illumination fibers 3a, 3b, 3c, . . . 3n. The transmitted light is communicated on the respective illumination fibers 3a to 3n to measurement units 12a to 12n. In each measurement unit 12a to 12n, the transmitted light passes through a series of polarizers, lenses and prisms before exiting. The exiting light illuminates the areas of living tissue under examination. Interacted light from the illuminated tissue mucosa is correspondingly detected by the measuring units 12a to 12n. In each measurement unit 12a to 12n, received interacted light passes through the measurement unit prism, lens, and polarizer as seen in FIG. 3 and is transmitted via collectors 7a and 7b back to spectroscope 9 for analysis.

Figure 2:
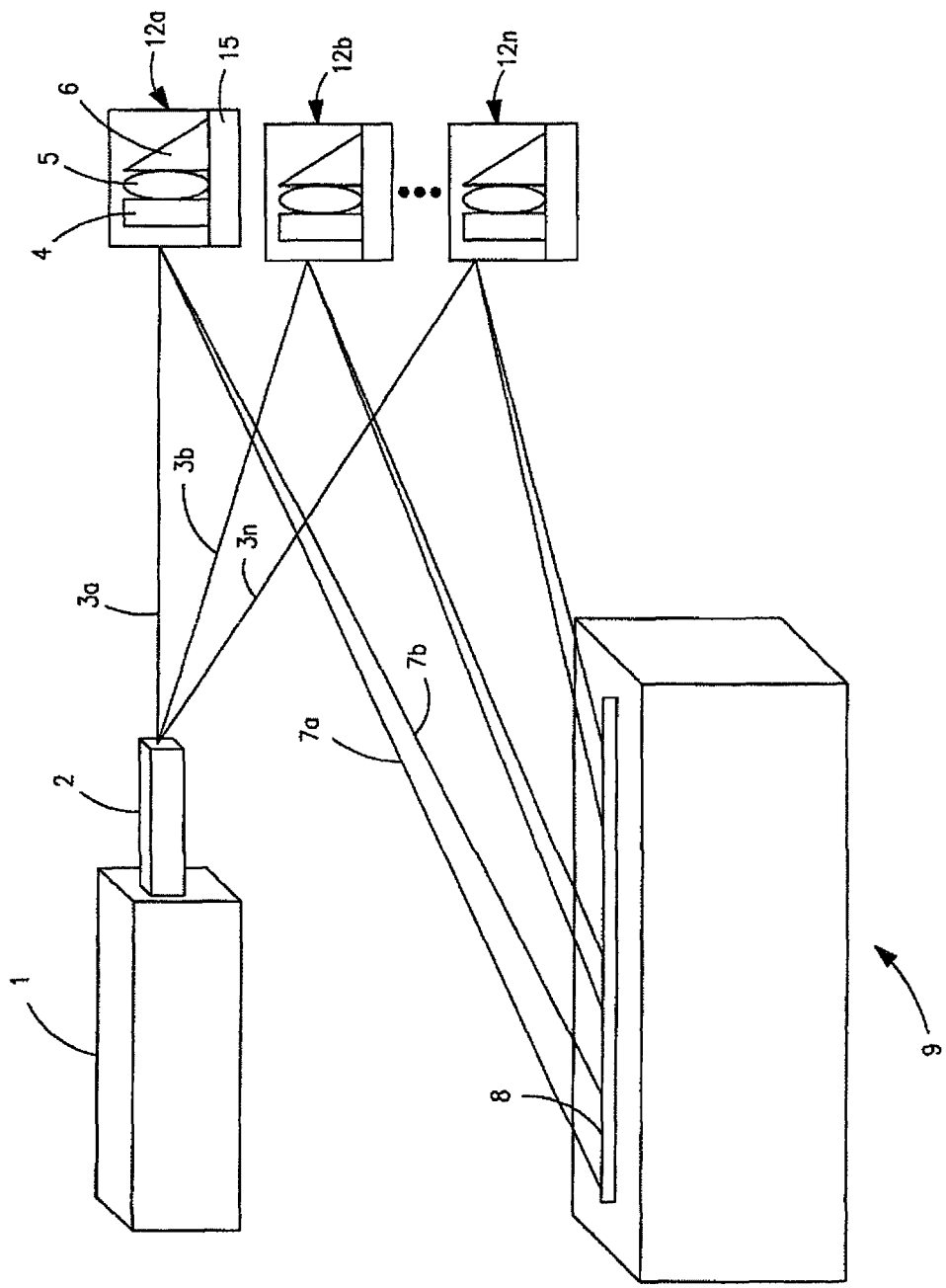
FIG. 2 illustrates an exemplary diagram of a system in accordance with the invention utilizing at least three optical blood content detectors.

FIG. 2 depicts a block diagram of an exemplary configuration of the system 100 of FIG. 1. Referring to FIG. 2, the exemplary system seen in FIG. 2 contains light source 1 for generating light of sufficient intensity and frequency to illuminate the tissue under investigation so as to ascertain the blood content within the illuminated tissue mucosa. Single fiber rod 2 may be, for example, a fiber optic conductor containing a optical core or similarly designed to equalize and collimate the light emitted from light source 1 to ensure uniform intensity and frequency of the light entering the illumination fibers. Illuminator fibers 3a-3n are individual optical transmission lines that convey the light from single fiber rod 2 to the measurement units 12a-12n. Light source 1 may be, for example, a xenon lamp, a halogen, lamp, an LED, or any other light source capable of providing a light of adequate intensity and frequency.

In addition to light source 1, measurement units 12a-12n further includes polarizer 4, lens 5, prism 6 and measurement window 15. Polarizer 4 is a linear polarizer designed to ensue that the transmitted light waves are aligned in a linear fashion, i.e., horizontally or vertically. Lens 5 is an optical lens that conveys light waves in a parallel orientation. Light waves exit lens 5 in a generally parallel direction and strike the surface of prism 6. Prism 6 is a optical prism with a coated reflective surface. Light waves striking the surface of prism 6 are orthogonally reflected through measurement window 15 into the underlying living tissue. Measurement window 15 is an optical window typically, glass or other transmissive material in the detection wavelength range, that does not adversely interact with or attenuate transmitted or reflected light waves.

Light that interacts with or is reflected off of the underlying tissue is conveyed through window 15 back through prism 6, lens 5 and polarizer 4 onto collectors 7a and 7b. Optical fibers 7a and 7b each convey the reflected light back to spectroscope processing unit (spectroscope) 9. It should be noted that as a result of the placement of optical collectors 7a and 7b with respect to polarizer 4, optical fibers 7a and 7b convey either horizontally or vertically polarized light waves back to spectroscope 9. Fibers 7a and 7b enter spectroscope 9 at slot 8 and convey there respective blood content data to the data receiver located in spectroscope 9.

An exemplary detailed operation of the system 100 is now described with respect to a single measurement unit 12a with regard to FIGS. 1 and 2. However, it shall be understood that this operation may be carried out simultaneously or otherwise by the measurement units 12a-12n depicted in FIG. 1. Referring to FIG. 2, light emitted from light source 1 passes through single fiber rod 2 to reach the individual optical fibers 3. As light emanating from light source 1 passes through single fiber rod 2, the rod 2 equalizes and collimates the intensity and wavelength of the light emitted from light source 1 and guides the equalized and collimated light into the individual illuminator fibers 3a to 3n.

Once the collimated light enters a single fiber 3a to 3n it is communicated to the individual measurement units 12a to 12n. Each measurement unit 12a to 12n is comprised of a illuminator fiber, a polarizer unit 4, a lens 5, a prism 6, and window 15. The transmitted light exits the measurement unit 12a via window 15 and illuminates a region of tissue within the living body.

Certain light interacted with the illuminated tissue is reflected back and collected by the corresponding measurement unit 12a to 12n through its corresponding window 15 and passes back through prism 6, lens 5, and polarizer unit 4 to the collector fibers 7a and 7b.

Each measurement unit 12a to 12n has two optical receiving or collector fibers 7a and 7b that direct the received or collected interacted light to pass-through slit 8 in spectroscope 9 for analysis. As an alternative to the receiving fibers 7a and 7b of measurement units 12a to 12n, directly entering spectroscope processing unit 9 via a slit 8, a lens may be provided between receiving fibers 7a and 7b and the slit 8 for an improved and more efficient light transmission. An exemplary configuration for such a lens is cylindrical. However, alternative shapes or other configurations may be employed in accordance with the invention.

Figure 14:
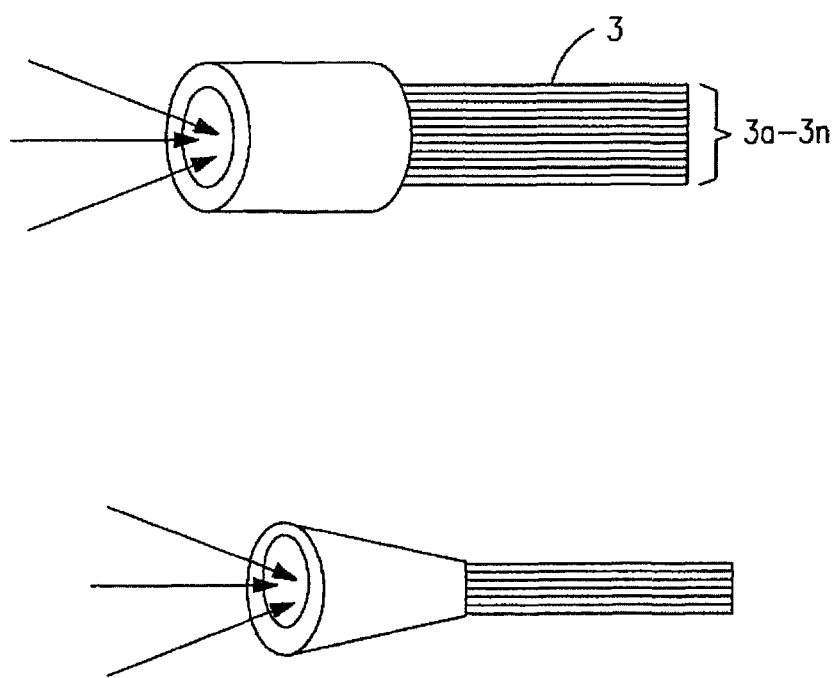
FIG. 14 illustrates an exemplary light fiber bundle useable with the present invention.

As depicted in and later described with respect to FIG. 14, individual fibers 3a to 3n may have a diameter as small as, for example, 100 μm, resulting in a fiber bundle 3 in FIG. 1 as small as 1 mm. In this example, the diameter of a single fiber should likewise be of sufficient size to receive light emitted from light source 1 to produce light emitted from the various windows of a desired intensity. In order to maintain each fiber bundle 3a-3n of sufficiently small size, each individual fiber end may have a tapered shape and the area of the core at the end face close to the light source is greater than that of the other end face close to the respective single measurement unit 12a-12n.

FIG. 3 depicts an exemplary configuration of measurement unit 12a. Other measurement units 12b to 12n may contain similar optical configurations. Referring to FIG. 3, Measurement unit 12a contains illumination fibers, and collector fibers, linear polarizer 41 and 42, lens 5, prism 6, and measurement window 15.

In operation of the measurement unit of FIG. 3, light emitted from light source 1 (shown in FIGS. 1 and 2) travels through illumination fiber 3 and passes through linear polarizer 4. Polarizer 4 is comprised of two linear polarizers 41 and 42. Linear polarizer 41 may be oriented for polarization in a horizontal direction and linear polarizer 42 may be oriented for polarization in a perpendicular direction relative to the linear polarization produced by polarizer 41. The transmitted linear polarized light beams 301 pass through linear polarizer 41 and enter lens 5. Due to the shape of lens 5, the light beams 301 exit the lens parallel to each other before being refracted by prism 6. The light is reflected off prism surface 21 and is conveyed through window 15 and illuminates the target tissue mucosa 17. Prism surface 21 may contain, for example, a vapor-deposited coating of silver, aluminum, or other material in order to produce the preferred reflectivity.

In the instance when window 15 is in contact with the target tissue mucosa 17, the transmitted light is interacted with by the tissue mucosa 17. Portions of the interacted light 302 and 303 reenter prism 6 and again refracted off of the prism surface 21 and back through lens 5. The interacted light 302 and 303 passes through lens 5 and into polarizer unit 4, passing through either linear polarizer 41 or linear polarizer 42. After passing through the respective polarizer 41 or 42, the light 302 and 303 enters the respective collector fibers 7a or 7b depending on which linear polarizer 41 or 42, the light has passed through.

Because of this lens, prism, and polarizer unit configuration, only light that interacts with tissue mucosa 17 at specific angles enters the collectors or receiving fibers 7a and 7b. More specifically, light entering collector or receiving fiber 7a is oriented at the same polarization direction as the transmitted light, since both transmitted and reflected light are passing though linear polarizer 41. In contrast, the light entering collector or receiving fiber 7b is always perpendicular to the transmitted light since it passes through linear polarizer 42 which is oriented in a perpendicular direction relative to that of liner polarizer 41.

Figure 4:
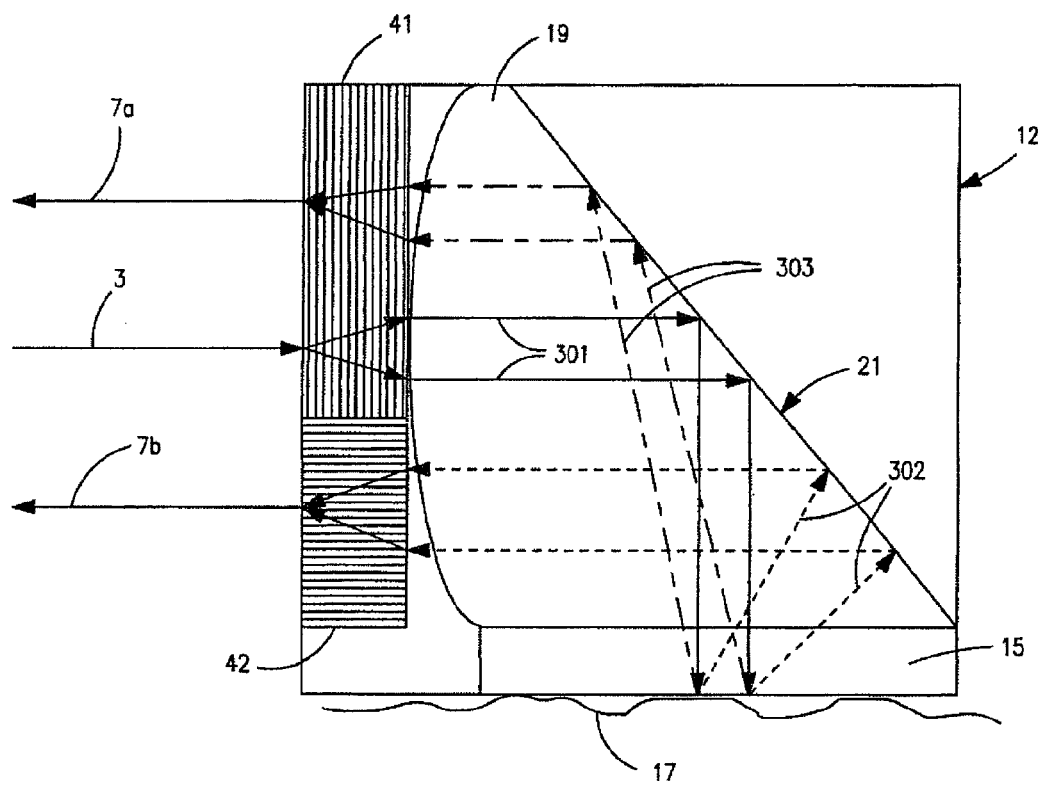
FIG. 4 illustrates an alternative exemplary embodiment of the optical blood content sensor useable with the present invention.

FIG. 4 depicts an alternative embodiment of the polarizer, lens, prism combination of measurement unit 12 of FIG. 3. In FIG. 4, the lens 5 and the prism 6 of FIG. 3 are integrated into a single lens prism unit 19. The integration of the two components decreases the number of sides the individual lens and prism combination has, thereby reducing the amount of stray light generated by reflection on the sides and accordingly, the stray light that reaches the light receiving fibers. A further advantage of utilizing a single lens prism combination may be realized due to the reduced number of optical components required, the reduced cost in manufacturing and assembly. In another embodiment, the flat reflection surface 21 of the prism may be spherical or ellipsoidal so as to achieve the same effect as the lens itself, thereby further reducing the number of components and manufacturing costs.

In operation, the measurement unit of FIG. 4 operates in a similar manner to that described with respect to FIG. 3. Light emitted from light source 1 travels through illuminator fiber 3 and passes through linear polarizer 41. Linear polarizer 41 may be oriented for polarization in a horizontal direction and linear polarizer 42 may be oriented for polarization in a perpendicular direction relative to the linear polarization produced by polarizer 41. The transmitted linear polarized light beams 301 pass through linear polarizer 41 and enter lens prism unit 19. Due to the shape of the lens portion of lens prism unit 19, light beams 301 are oriented parallel to each other before being refracted by surface 21 of lens prism unit 19. The light is reflected off surface 21 and is conveyed through window 15 and illuminates the target tissue mucosa 17. Prism surface 21 may contain, for example, a vapor-deposited coating of silver, aluminum, or other material in order to produce the preferred reflectivity.

In the instance when window 15 is in contact with the target tissue mucosa 17, the transmitted light interacts with the tissue mucosa 17. Portions of the interacted light 302 and 303 reenter lens prism unit 19 and are again refracted off of surface 21 and back through the lens portion of lens prism unit 19. The light 302 and 303 pass through lens prism unit 19 and into either linear polarizer 41 or linear polarizer 42. After passing through the respective polarizer 41 or 42, the light enters the respective collectors or receiving fibers 7a or 7b, accordingly.

Because of the configuration of lens prism unit 19 and polarizer units 41 and 42 only light that interacts with tissue mucosa 17 at specific angles enters the collectors or receiving fibers 7a and 7b. More specifically, light entering receiving fiber 7a is oriented at the same polarization direction as the transmitted light, since both transmitted and reflected light are passing though linear polarizer 41. In contrast, the light entering receiving fiber 7b is always perpendicular to the transmitted light since it passes through linear polarizer 42 which is oriented in a perpendicular direction relative to that of liner polarizer 41.

Figure 5:
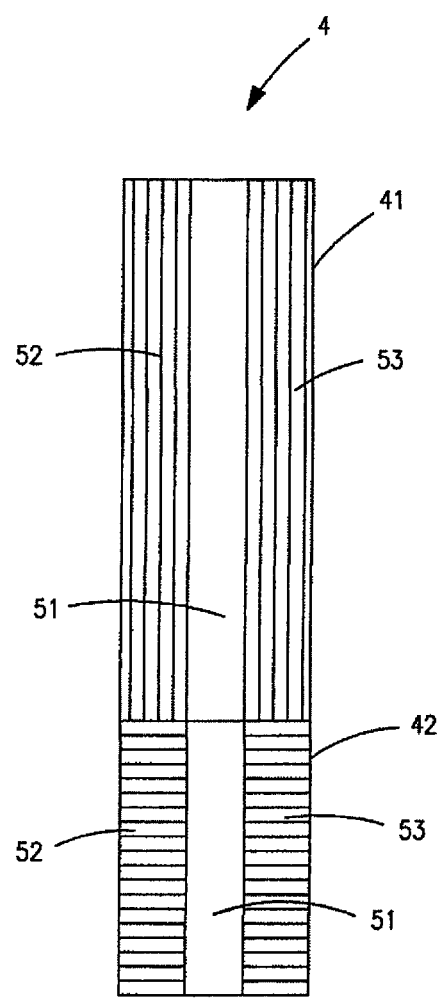
FIG. 5 illustrates an exemplary embodiment of a polarizer useable with the present invention.

FIG. 5 depicts an exemplary configuration of the linear polarizer unit 4 of FIGS. 2-4. FIG. 5 illustrates that the linear polarizers 41 and 42 of FIGS. 2 through 4 may be composed of a glass substrate 51 with a polymer material 52 bonded to a first side and an aluminum wire vapor-deposited on an opposite, second side 53. The polarizing surfaces i.e., polymer side or aluminum-wire side, may preferably be bonded on the surface of the light receiving fibers. Due to the thermostability of the polarizing surface, the surface is preferably formed from an aluminum wire, such as, for example, the aluminum-wire grid polarizing filter manufactured by Edmunds Optics Inc. of Barnington, N.J.

Figure 6:
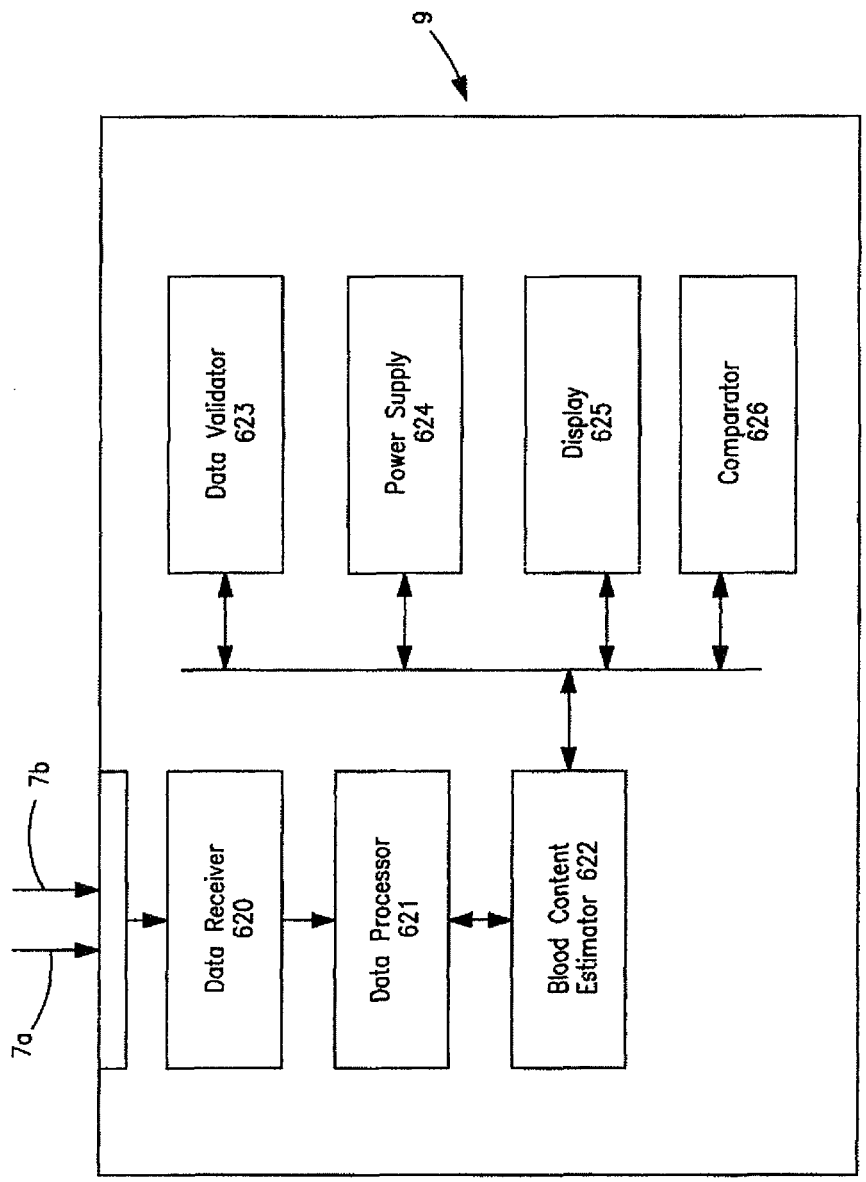
FIG. 6 illustrates a representative block diagram of a exemplary processor useable with the present invention.

In the present invention, calculations are computed based on the detection of interacted light received by each individual measurement unit. FIG. 6 shows a schematic diagram of an exemplary spectroscope 9. In FIG. 6, the spectroscope 9 includes a data receiver 620, a data preprocessor 621, a blood content estimator 622 (or blood content calculator), a data validator 623, a power supply 624, an optional display or indicator 625 and a data comparator 626. Data receiver 620 receives information from the receiving fibers 7a and 7b.

In operation, the data received by the data receiver 620 of the spectroscope 9 in FIG. 6 is provided to a data preprocessor 621. The data preprocessor 621 executes, for example, a data correction algorithm, such as white correction represented in the following equation (1).

$$\Delta Ic(\lambda) = \frac{\Delta I(\lambda)}{\Delta Iw(\lambda)} = \frac{I_\Pi(\lambda) - I_\perp(\lambda)}{Iw_\Pi(\lambda) + I_\perp(\lambda)} \qquad (1)$$

Where the symbols Π and ⊥ used in the numerator and denominator of equation (1) represent the spectrum of horizontally polarized light and the spectrum of vertically polarized light, respectively. In equation (1), $\lambda$ represents wavelength, $\Delta I(\lambda)$ indicates the measured difference polarization spectrum, $\Delta Iw(\lambda)$ is the spectrum measured using a standard white plate and is calculated by summing the white horizontal polarization spectrum $Iw_\Pi(\lambda)$ and the white perpendicular polarization spectrum $Iw_\perp(\lambda)$, as shown in the denominator of equation (1). In the numerator of equation (1), the difference between the horizontal polarization spectrum $I_{\Pi}(\lambda)$ and the perpendicular polarization spectrum $I_\perp(\lambda)$ is calculated and a signal indicative of $\Delta I(\lambda)$.

Based on the generated results of the data processor 621, the blood content estimator 622 calculates the blood content by using equation (2) below, which is shown in, for example, M. P. Siegel et al. *Assessment of blood supply in superficial tissue by polarization-gated elastic light-scattering spectroscopy*, Applied Optics, Vol. 45, Issue 2, pp. 335-342 (2006), which is incorporated by reference herein.

$$\Delta I(\lambda) = \Delta I_{scattering}(\lambda) \exp[-\alpha A_{PG}(\lambda)] \quad (2)$$

The blood content estimator 622 calculates the blood quantity by using a model equation, such as equation (2), and may provide a corresponding blood content value to optional display 625. Alternatively, the blood content estimator 622 may also provide the blood content value to data validator 623 as a check on the integrity of the collected data. Further, blood content estimator 622 may provide the results from the various detection units to comparator unit 626 to determine the validity of a measurement and to improve the accuracy of detection based on the numerous measurement units.

Figure 7:
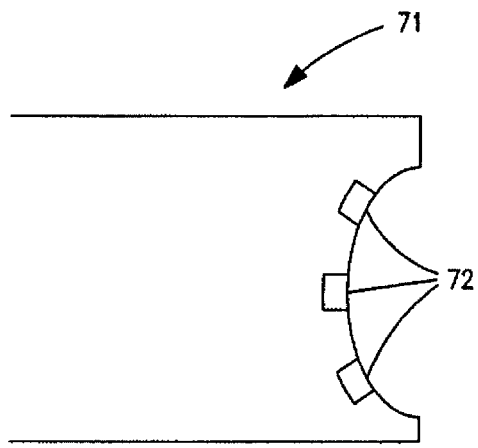
FIG. 7 illustrates an exemplary embodiment of a first endoscope configuration utilizing the present invention.

Various configurations of exemplary endoscopes with multiple measurement units in accordance with the invention are depicted in FIGS. 7 to 13. More specifically, FIG. 7 depicts an endoscope tip 71 with multiple measurement units. Endoscope tip 71 is generally concave in shape with the multiple measuring units 72 deployed along the concave surface of the tip. In operation, by pressing an endoscope tip 71 into living tissue, the tissue is drawn into, or aspirated into contact with the multiple measuring units 72. The placement of numerous measurement units on the concave surface ensures contact by one or more of the measurement units. Contact with multiple measurement units would tend to provide a more accurate reading than a probe with a single measurement unit. In additional, greater accuracy in blood content detection is achievable by comparing the data obtained from the multiple measuring units 72.

Figure 8:
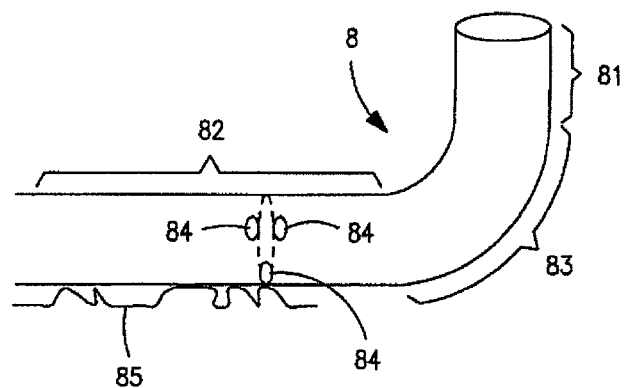
FIG. 8 illustrates an exemplary embodiment of a second endoscope configuration utilizing the present invention.

In the configuration of FIG. 8 multiple measurement units 84 are employed with a traditional flexible endoscope 8. Endoscope 8 contains a rigid tip 81, a connecting portion 82, angled portion 83, and measurement units 84 in accordance with the invention. By placing the measurement units 84 on the outer circumference of the insertion portion of the flexible endoscope, the detection windows are advantageously more likely to contact the tissue mucosa upon insertion and removal of the device.

Figure 9:
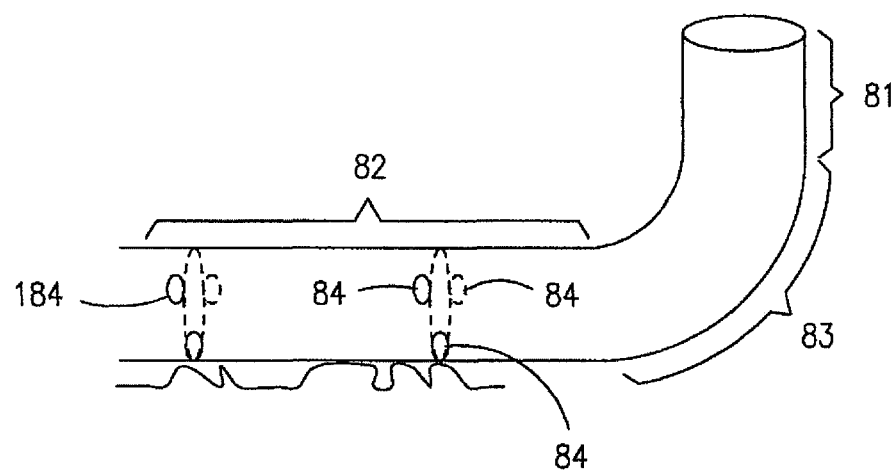
FIG. 9 illustrates an exemplary embodiment of a third endoscope configuration utilizing the present invention.

FIG. 9 depicts a variation of the configuration of the invention shown in FIG. 8. A second ring of detection units 184 is longitudinally located on the circumference of the connecting portion 82. By utilizing a second ring of measurement units 184 on the circumference of the flexible endoscope, a user is able to obtain measurement results at two different locations along the longitudinal access of the endoscope. By analyzing the data from the two different regions on the living tissue, an operator can more accurately determine the proximity of the abnormal lesion by utilizing the differences between the two areas of measurement.

Figure 10:
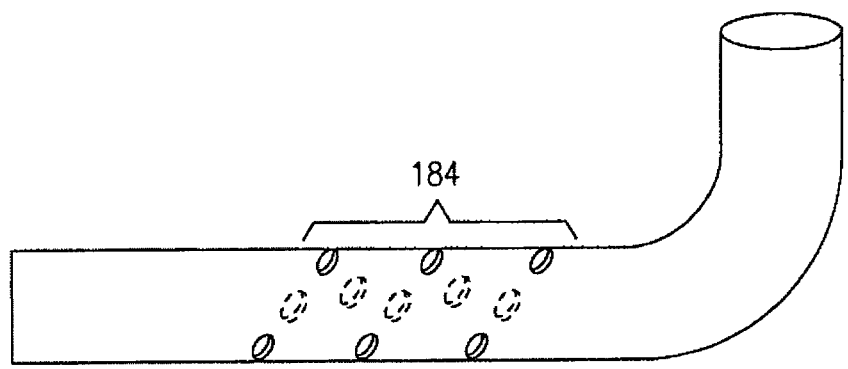
FIG. 10 illustrates an exemplary embodiment of a fourth endoscope configuration utilizing the present invention.

FIG. 10 depicts an alternative embodiment to those disclosed in FIGS. 8 and 9. As seen in FIG. 10, the measurement units 184 may be arranged in a substantially helical arrangement about the circumference of the insertion portion of a flexible endoscope. Such an arrangement significantly increases the coverage area of the multiple detection windows.

Figure 11:
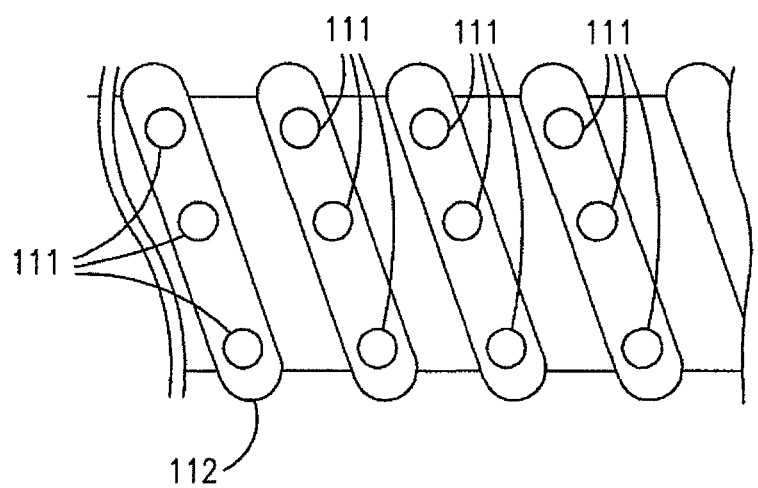
FIG. 11 illustrates an embodiment of an exemplary portion of an endoscope utilizing the present invention.

FIG. 11 depicts an embodiment of the present invention wherein the connecting portion of the endoscope has a thread-like or helical protruded portion 112. In this embodiment, the multiple measurement units 111 are placed in the outer circumference of the helical protrusion 112. In operation of this configuration, the multiple measurement units 111 tend to serially come into contact with the same areas of tissue mucosa as the insertion portion is rotated upon insertion or extraction.

Figure 12:
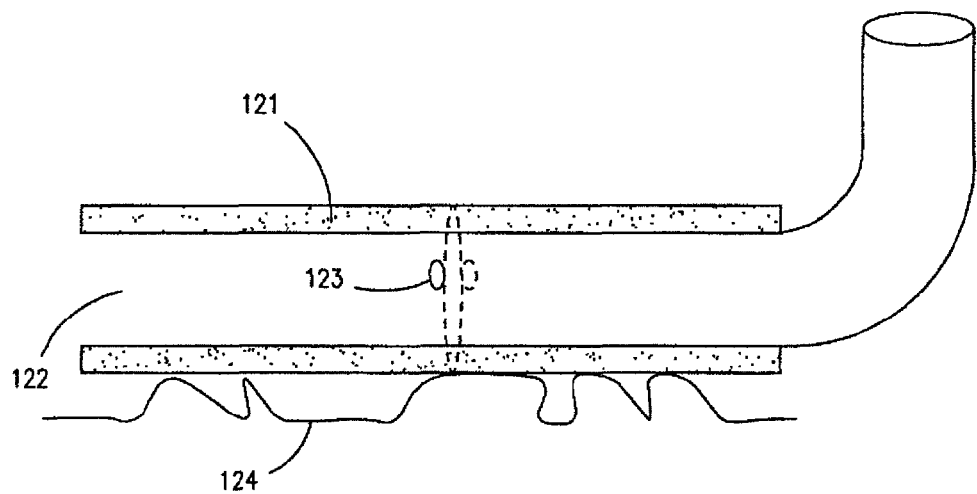
FIG. 12 illustrates an exemplary endoscope and sheath configuration utilizing the present invention.

FIG. 12 depicts an endoscope 122 covered by a sheath 121 with measurement units 123 disposed therein. Sheath 121 is essentially a tube into which, for example, an endoscope 122, such as a conventional endoscope is inserted. Multiple measurement units 123 are arranged along the circumference of sheath 121 and contact living tissue mucosa 124. This type of sheath configuration allows the user to employ a conventional endoscope while at the same time advantageously utilizing blood content detection methods for guiding the endoscope to abnormal tissue. It will be appreciated by one skilled in the art that sheath 121 may also be configured with the thread-like protrusions 112 and the multiple measurement units 123 may likewise be configured in a spiral configuration along the circumference of the thread-like shape.

Figure 13:
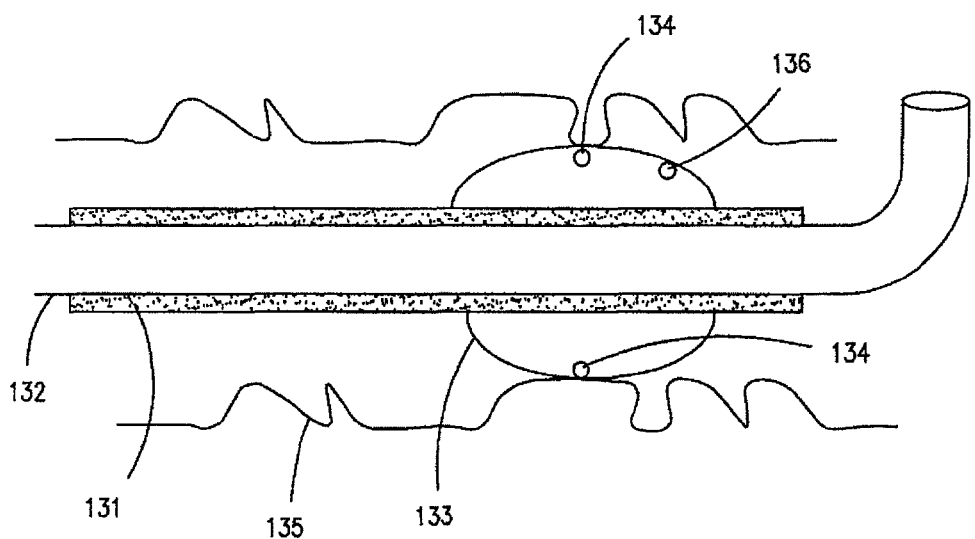
FIG. 13 illustrates a second exemplary endoscope and sheath configuration utilizing the present invention.

FIG. 13 depicts an embodiment with sheath 131, endoscope 132, and balloon 133 having multiple measurement units 134 disposed therein. Sheath 131 is typically a hollow tube through which, for example, a endoscope 132 will be inserted. Balloon 133 is attached to or formed integral with the sheath 131 and is inflated by either air or water pressure. Upon placement of sheath 131, balloon 133 is inflated to contact the target tissue mucosa 135. The inflation of balloon 133 ensures contact between the multiple measurement units 134 and tissue mucosa 135. Further, a sensor 136 may be employed to start the blood detection process based on inflation of balloon 133. As will be appreciated by those skilled in the art, sensor 136 may be located internally or externally to the sheath 131 or balloon 133. For example a sensor could be located on the surface of balloon 136 or within sheath 131 and may sense the back pressure exerted by the balloon 133 when it inflates and contacts living tissue 135.

In an alternative embodiment, two or more balloons may be utilized, each with its own set of measurement units 134. By utilizing multiple balloons 133, the multiple measurement units 134 can be spread out along sheath 131. In the manner, the blood content detection data can be analyzed to determine which of the balloons 133 is closest to an area of interest. Such information will aid in isolating and detecting potential areas of interest.

In another exemplary embodiment of the present invention, blood data collection is triggered upon the sensing of contact between balloon 133 and tissue mucosa 135. Such sensing of contact may be the result of back pressure sensed in the balloon inflation mechanism or as a result of surface sensors 136 located in balloon 133.

While the foregoing description and drawings represent the preferred embodiments of the present invention, it will be understood that various changes and modifications may be made without departing from the spirit and scope of the present invention. For example, although the improved method and apparatus described herein as part of or in conjunction with an endoscope, it is also possible to use the invention with a stand alone probe or other medical device.

What is claimed is:

1. An apparatus that comprises:
   a cylindrically-shaped probe that has a circumference, wherein said cylindrically-shaped probe comprises:

a plurality of measurement units outwardly disposed circumferentially along and in a raised helical portion of an outer surface of said cylindrically-shaped probe, said plurality of measurement units thereby arrayed in a substantially helical arrangement, wherein said raised helical portion is sufficiently large to contact a tissue that forms an intended cavity of a living body; wherein each of the plurality of measurement units includes one of a plurality of illuminators and one of plurality of collectors, and a processing unit coupled to the plurality of measurement units, wherein each of the plurality of illuminators of the plurality of measurement units is configured to illuminate a different tissue region within a living body, each of the plurality of collectors is configured to collect interacted light detected by a corresponding one of the plurality of measurement units from one of the different tissue regions illuminated by a corresponding one of the plurality of illuminators, and to transmit the collected interacted light to the processing unit, a blood content estimator of the processing unit configured to generate a signal indicative of blood content measurement, and an indicator is coupled to the processing unit to indicate a parameter based on signals from the plurality of measurement units and configured to guide said cylindrically-shaped probe through a cavity of the living body to locate abnormal tissue.

2. The apparatus of claim 1 wherein the processing unit further comprises:

a comparator that compares signals indicative of light interacted with a tissue region for the plurality of measurement units, and that generates at least one comparison signal, wherein the blood content estimator is configured to calculate information indicative of the blood content in an illuminated tissue based on the at least one comparison signal.

3. The apparatus of claim 1 wherein each of the plurality of illuminators emits collimated light.

4. The apparatus of claim 3 wherein each of the plurality of illuminators emits polarized light.

5. The apparatus of claim 1 that further comprises at least one polarizer proximate to a corresponding one of the plurality of collectors.

6. The apparatus of claim 5 wherein at least one of the plurality of measurement units includes two polarizers located proximate to a corresponding one of the plurality of collectors and wherein the two polarizers have substantial orthogonal polarizations to one another.

7. The apparatus of claim 1 that further comprises an endoscope.

8. The apparatus of claim 7, wherein the plurality of measurement units are positioned proximate a distal tip of the endoscope.

9. The apparatus of claim 1 wherein each of the plurality of illuminators comprises one of a plurality of first optical fibers through which light from a light source passes to illuminate one of the different tissue regions, and each of the plurality of collectors comprises one of a plurality of second optical fibers to receive interacted light from one of the different tissue regions.

10. The apparatus of claim 9 wherein each of the plurality of measurement units includes an optical system to direct the light from a corresponding one of the plurality of first optical fibers and to direct light to a corresponding one of the plurality of second optical fibers.

11. The apparatus of claim 1 wherein the processing unit comprises a comparator that compares the signals generated substantially simultaneously by the plurality of measurement units, and that generates at least one corresponding comparison signal, said processing unit further including a blood content estimator configured to calculate information indicative of the blood content in an illuminated tissue based on the comparison signal.

12. An apparatus configured to determine a characteristic of a living tissue that forms a cavity of a living body, wherein the apparatus comprises:

a cylindrically-shaped probe configured to be inserted into a cavity of a living body, including:

an outer surface of said cylindrically-shaped probe that has a plurality of measurement units outwardly disposed thereon, the plurality of measurement units disposed circumferentially along and in a raised helical portion of said outer surface of said cylindrically-shaped probe, said plurality of measurement units thereby arrayed in a substantially helical arrangement, wherein said raised helical portion is sufficiently large to contact a tissue that forms an intended cavity of a living body and facilitate contact between said plurality of measurement units and said tissue, wherein each of the plurality of measurement units includes one of a plurality of illuminators and one of a plurality of collectors, and a processor coupled to the plurality of measurement units, wherein each of the plurality of illuminators is configured to illuminate a different portion of tissue within the living body, each of the plurality of collectors is adapted to collect interacted light detected by a corresponding one of the plurality of measurement units from one of the different portions of tissue illuminated by a corresponding one of the plurality of illuminators and to transmit the collected interacted light to the processor, and the processor includes a blood content estimator configured to provide an indication of blood content within illuminated tissue to guide said cylindrically-shaped probe.

13. The apparatus of claim 12 wherein each of the plurality of illuminators comprises one of a plurality of first optical fibers through which light from a light source passes to illuminate one of the different tissue regions, and each of the plurality of collectors comprises one of a plurality of second optical fibers to receive interacted light from one of the different tissue regions.

14. The apparatus of claim 13 wherein each of the plurality of measurement units includes an optical system to direct the light from a corresponding one of the plurality of first optical fibers and to direct light to a corresponding one of the plurality of second optical fibers.

15. An apparatus for use within a cavity of a living body, wherein the apparatus comprises:

an endoscope;

a sheath to receive the endoscope, wherein said sheath has an inner surface and an outer surface with a raised helical portion;

a plurality of measurement units outwardly disposed circumferentially along and in said raised helical portion on the outer surface of the sheath, said plurality of measurement units thereby arrayed in a substantially helical arrangement, wherein each of the plurality of measurement units includes one of a plurality of illuminators and one of a plurality of collectors, and a processing unit coupled to the plurality of measurement units, wherein each of the plurality of illuminators of the plurality of measurement units is configured to illuminate a different region of tissue within the living body, each of the plurality of collectors is configured to collect interacted light from a corresponding one of the plurality of measurement units that detected the interacted light from one of the different tissue regions illuminated by a corresponding one of the plurality of illuminators, said collector being configured to transmit the collected interacted light to the processing unit;

the processing unit includes a blood content estimator that is configured to determine blood content within illuminated tissue regions based on the signals transmitted by the plurality of collectors; and an indicator coupled to the processing unit is configured to indicate a parameter based on the determined blood content to guide the endoscope through the cavity of the living body to locate abnormal tissue.

16. The apparatus of claim 15 wherein an outer circumference of the sheath is larger than the cavity of a living tissue.

17. The apparatus of claim 15, wherein the apparatus further comprises a sensor to detect contact between the sheath and tissue that forms the cavity of the living body.

18. The apparatus of claim 17 wherein at least one of the plurality of measurement units are energized in accordance with a received signal from the sensor.

19. The apparatus of claim 15 wherein each of the plurality of illuminators comprises one of a plurality of first optical fibers through which light from a light source passes to illuminate one of the different tissue regions, and each of the plurality of collectors comprises one of a plurality of second optical fibers to interacted light from one of the different tissue regions.

20. The apparatus of claim 19 wherein each of the plurality of measurement units includes an optical system to direct the light from a corresponding one of the plurality of first optical fibers and to direct light to a corresponding one of the plurality of second optical fibers.

21. A method for guiding an endoscope within a cavity of a living organism, wherein the method comprises the steps of:

providing said endoscope with a plurality of measurement units disposed circumferentially along and in a raised helical portion on an outer surface of the endoscope, said plurality of measurement units thereby arrayed in a substantially helical arrangement, wherein each of the plurality of measurement units includes one of a plurality of illuminators and one of a plurality of collectors;

inserting the endoscope into the cavity of the living organism, contacting the endoscope with a surface of tissue that forms the cavity;

illuminating different portions of a contacted tissue surface through said plurality of illuminators;

detecting interacted light from an illuminated tissue surface through one of said plurality of measurement units;

collecting said detected interacted light by the one collector of the one measurement unit;

transmitting the collected light by the one collector to a processing unit;

processing said received interacted light by a blood content estimator of the processing unit to determine a parameter indicative of blood content of the illuminated tissue; and guiding the endoscope through said cavity based on said parameter to locate abnormal tissue.

22. The method of claim 21 wherein said helical portion is provided on an outer circumference of an inflatable cuff surrounding said endoscope and the contacting step is achieved by inflating said inflatable cuff.

23. The method of claim 21, wherein the method further comprises the steps of repositioning the endoscope within the living body based on a determined parameter.

* * * * *